United States Patent [19]
Millar et al.

[11] Patent Number: 6,052,177
[45] Date of Patent: *Apr. 18, 2000

[54] APPARATUS USED IN DETERMINING THE DEGREE OF COMPLETION OF A PROCESSED MEDIUM

[75] Inventors: Ord D. Millar, Pierrefonds, Canada; Richard J. Van Fleet, Cave Creek, Ariz.

[73] Assignee: Honeywell Inc., Minneapolis, Minn.

[*] Notice: This patent is subject to a terminal disclaimer.

[21] Appl. No.: 08/988,972

[22] Filed: Dec. 11, 1997

[51] Int. Cl.[7] .................................................. G01N 21/64
[52] U.S. Cl. ............................ 356/73; 356/425; 356/318
[58] Field of Search ............................ 356/73, 425, 318; 162/49, 263

[56] References Cited

U.S. PATENT DOCUMENTS

| | | | |
|---|---|---|---|
| 3,994,602 | 11/1976 | Howarth | 356/435 |
| 4,222,064 | 9/1980 | Lodzinski | 356/73 |
| 5,220,172 | 6/1993 | Berthold et al. | 250/461.1 |
| 5,486,915 | 1/1996 | Jeffers et al. | 356/318 |

*Primary Examiner*—Frank G. Font
*Assistant Examiner*—Zandra V. Smith
*Attorney, Agent, or Firm*—Anthony Miologos

[57] ABSTRACT

An apparatus is disclosed that develops output signals representing the degree of finished state of a processed medium during a process operation, such as the lignin content of wood pulp during delignification or, alternatively, the brightness during the bleaching process. Broad spectrum light energy from a light energy source is injected into the processed medium and the resultant reflected light energy is collected from a first light collector located near the point of injection and a second light collector located far from the point of injection. The light energy collected by each light collector is conveyed to a respective light analyzer associated with each light collector. Each light analyzer divides the detected light into distinct spectral wavelengths and generates output signals representing the intensity of light energy received in each wavelength. A feedback arrangement conducts the light energy emitted by the source to a location proximate the point of injection and then to a light analyzer. The light analyzer associated with the feedback arrangement divides the light emitted by the light source into distinct spectral wavelengths and generates output signals representing the intensity of the light energy emitted by the source in each wavelength. The output signals can be used by a process monitoring system to examine the degree of finished state of the processed medium.

11 Claims, 4 Drawing Sheets

APPARATUS USED IN DETERMINING THE DEGREE OF COMPLETION OF A PROCESSED MEDIUM

CROSS-REFERENCE TO RELATED APPLICATIONS

The present application is related to co-pending application Ser. No. 08/989,720, titled "A Continuous In-Line Kappa Measurement System" and co-pending application Ser. No. 08/088,971, titled "A Method for Producing Continuous In-Line Kappa Measurements for Papermaking Pulps"; both applications filed on the same date herewith, and both applications having a common assignee as the present invention.

FIELD OF THE INVENTION

This invention relates in general to an apparatus used in determining the degree of completion of a processed medium and, more specifically, to an apparatus for producing output signals representing the degree of process completion of papermaking pulps.

BACKGROUND OF THE INVENTION

In the pulp and paper industry, pulping refers to the process of converting wood chip feed stock into separate fibers by the chemical reaction between the lignin found in the wood chips and the active chemicals in a cooking liquor. This delignification process separates the wood cellulose fibers by breaking down the lignin. Lignin is a polymer of complex chemical structure which "cements" together the wood's cellulose fibers. The most prevalent method of delignification is by chemical means in which raw wood chips and chemicals are combined at a controlled pressure and temperature in a vessel known as a digester. While in the digester, the amount of lignin removed from the wood chips determines the product quality, the product yield, and the amount of energy consumed. Fluid drained from the digester during delignification contains lignin removed from the wood chips and is referred to in the industry as "black liquor". Black liquor is subsequently used to advantage during the pulping process as fuel in a boiler to produce process steam.

One common method of delignification presently used in pulp making is the kraft process. In this process, the wood chip feed stock is cooked with caustic soda and sodium sulfide, which removes most of the lignin without attacking the remaining cellulose fibers. When the remaining pulp of the kraft process is not passed through a bleaching process, it is used in cardboard or paper sack production. The dark color of this product is due to the remaining lignin in the fibers. However, if the final product of the process is to be a good-quality white paper, a bleaching step is introduced in the process using chlorine, chlorine dioxide, oxygen, ozone, or hydrogen peroxide as the bleaching agent. The bleaching dissolves the remaining lignin and renders white the remaining cellulose fibers. The amount of whiteness and the term or amount of time that the final paper product remains white are dependent on the remaining residual lignin in the cellulose fibers. It is, therefore, customary to test the lignin content of the pulp fibers and use this determination as a measure of the effectiveness of the ongoing bleaching operation.

Predicting the bleachability of the pulp in the prior art has been by the use of one or more of the several available tests such as the Permanganate Number (TAPPI method T-214), or the Kappa Number (TAPPI method T-236), or the Roe Chlorine Number (TAPPI method 202), etc. Each of these tests is designed to determine the quantity of lignin present in the pulp fibers as a group and provides an indication of the total bleach requirement (the oxidizing agent demand of the pulp) in the bleaching step. The most commonly used of these tests is the Kappa number, which refers to the amount of material remaining in the pulp after cooking that can be oxidized by a standard solution of potassium permanganate. The material is often equated with the lignin content of the fibers.

The Kappa number test, as well as the other tests noted, is most commonly carried out by laboratory analysis of hourly samples of the digester output (samples are typically obtained at the last stage of the brownstock washer). This requires extracting a representative sample of the pulp, separating the pulp fibers from the cooking liquor, drying the pulp to oven-dry conditions, re-suspending the fibers, and treating this new mixture with one or more special agents, all under strict laboratory conditions. The laboratory analysis of the residual lignin takes approximately one hour and, therefore, is a poor method for providing process control feedback and cannot be used for feedforward control. A number of automatic sampling and testing devices have been tried but they have been mostly unsuccessful in providing accurate long-term results and do not reduce the one-hour delay between process and measurement of the residual lignin.

Still other devices are known which use the ultraviolet (UV) fluorescence properties of lignin to measure the lignin concentration. Such testing systems require very dilute lignin solutions to be prepared prior to measurement and, therefore, are not suitable for in-situ, or real-time, testing. Other ultraviolet absorption testing methods have attempted to measure the residual lignin in wood pulp by sampling the pulp every few minutes, preparing and diluting the sample, and circulating the sample into a loop where the UV light absorption is measured over a prescribed time period and the pulp concentration is measured independently. Even though this system provides for a faster method of testing than that of the laboratory method, it is still off-line.

One system known which provides for in-situ lignin testing is taught by U.S. Pat. No. 5,486,915, issued on Jan. 23, 1996, to Jeffers et al. This lignin analyzer uses a fluorescence technique to measure lignin concentration in undiluted samples of wood pulp. This method and apparatus require the use of fairly complex detection methods that use the radiation of the wood pulp with excitation light in a specific wavelength (in the range of 337 nm) in order for the residual lignin in the pulp to emit fluorescence. A spectral distribution of the fluorescence emissions is then determined and output signals produced to a signal processor that quantifies the residual lignin in the pulp by either a wavelength centroid or band ratio method.

Even though this system provides for in-situ, real-time analysis of the lignin concentrations, it is more effective during the early stages of the bleaching process where greater concentrations of lignin are present. In the later stages of the bleaching process the lignin content is reduced appreciably, thereby diminishing the fluorescence emissions of the pulp. This method also does not lend itself to measuring the later stages of the pulp process involving the brightness processing of the pulp, important in the formation of quality paper products requiring a high brightness level. A balance of bleaching agent to brightness must be determined in order not to degrade the strength of the pulp, increase the cost of the bleaching operation, limit the exposure of personnel to toxic chemicals, and provide minimum impact on the environment.

SUMMARY OF THE INVENTION

Therefore, there is provided by the present invention an apparatus that develops output signals representing the degree of finished state of a processed medium during a process operation. The apparatus injects broad-spectrum light energy from a light energy source into the processed medium, or undiluted sample of the processed medium, and collects the resultant reflected light energy from a first light collector located near the point of injection and a second light collector located far from the point of injection. The light energy thus collected is conveyed to a respective light analyzer of a light analyzer array associated with each light collector. Each light analyzer divides the detected light into distinct spectral wavelengths and generates output signals representing the intensity of light energy received in each wavelength. A feedback arrangement conducts the light energy emitted by the light source to a location proximate the point of injection and then to an associated light analyzer in the light analyzer array. The light analyzer associated with the feedback arrangement divides the light emitted by the light source into distinct spectral wavelengths and generates output signals representing the intensity of the light energy emitted by the light source in each wavelength.

Accordingly it is an object of the present invention to provide an apparatus that develops output signals representing the degree of finished state of a processed medium.

It is another object of the present invention to provide an apparatus that can produce output signals representing the degree of finished state of a processed medium in-situ without dilution of the processed medium or the use of chemical laboratory testing.

It is still another object of the present invention to provide an apparatus that can produce output signals that may be used with a process control system to provide realtime, feed-forward control of the processing of the medium.

BRIEF DESCRIPTION OF THE DRAWINGS

Other objects, features, and advantages of the present invention will be apparent from the following description of a preferred embodiment thereof, taken in conjunction with the accompanying drawings, in which.

DETAILED DESCRIPTION OF THE INVENTION

Figure 1:
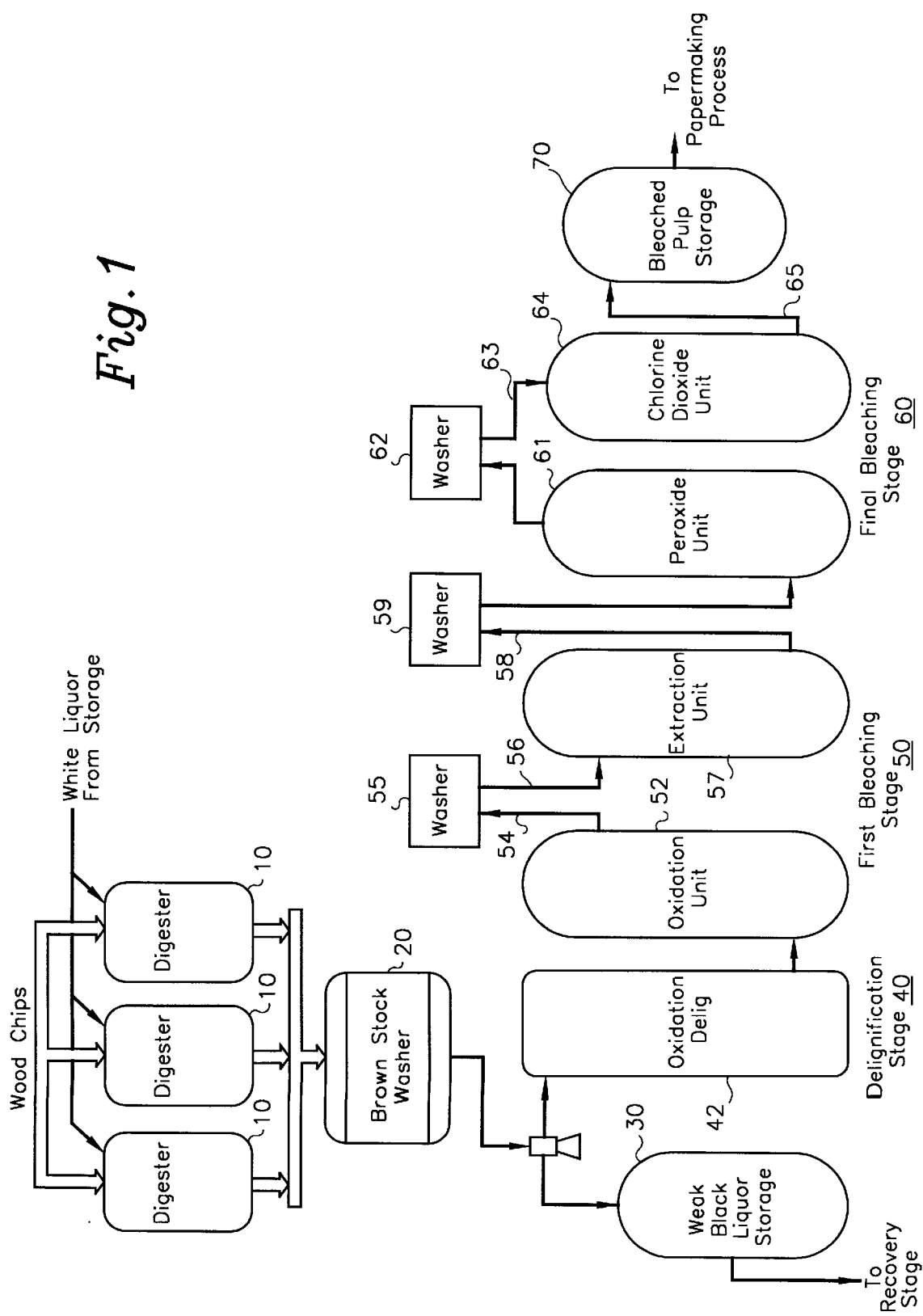
FIG. 1 shows a typical papermaking pulp process where the present invention is used to advantage.

Turning to FIG. 1, a typical process is shown for processing wood chips into papermaking pulp. Wood chips are fed into a plurality of digesters 10 along with a solution known as "white liquor". The white liquor in a kraft process is typically a mixture of sodium hydroxide (NaOH) and sodium sulfide ($Na_2S$). The wood chips and white liquor are cooked in the digesters 10 under controlled temperature and pressure to delignify or extract the binding agent, commonly known as lignin, from the cellulose fibers of the wood chips. Fluid drained from the digesters 10 during the delignification process is called "black liquor" and contains spent white liquor and lignin removed from the wood chips. This black liquor is removed by a one or more "brown stock" washers 20 prior to the pulp bleaching step. The black liquor at this stage is referred to as a "weak" black liquor and consists of sodium sulfate ($Na_2SO_4$), sodium carbonate ($Na_2CO_3$), sodium sulfide ($Na_2S$), and lignin organics. Weak black liquor is normally stored in containers 30 before being fed to a recovery operation.

A key element in the pulping manufacturing process is liquor recovery and power generation. Weak black liquor is fed to a system of multiple effects evaporators (not shown), where it is concentrated. This black liquor is then used as fuel in a furnace to manufacture steam for the papermaking pulp process and for power. A furnace recovery system (not shown) receives the smelt from the recovery furnace, which is dissolved into a "green liquor", clarified, and causticized with lime and sodium hydroxide (NaOH), to produce white liquor for the pulping process.

When the final product of the pulping process is to be a good-quality white paper, a bleaching process is introduced. The bleaching process varies according to the type of finished product the pulp is to become. Therefore, the number of bleaching stages in the bleaching process and the type of bleaching agents used control the "whiteness" of the finished paper product. Typically, the bleaching process employs a delignification stage 40 and one or more bleaching stages, such as the first bleaching stage 50 and final bleaching stage 60. Each bleaching stage introduces oxygen, chlorine, chlorine dioxide, ozone or some other bleaching agent to the pulp. For this example, the bleaching process begins by feeding the pulp from the brown stock washer 20 to an oxygen ($O_2$) delignification unit 42. This provides further removal of any residual lignin remaining in the pulp after digestion and black liquor removal by the brown stock washer 20. The pulp is then pumped to a first bleaching stage 50, consisting of an oxidation unit 52, a washer 55, and an extraction unit 57. The pulp is pumped to the washer 55 from the oxidation unit 52 via conduit 54 and from the washer 55 to the extraction unit 57 via conduit 56. Oxygen, chlorine dioxide, or other bleaching agents are introduced into the pulp in this stage to further the brightening process. The brightening agents are removed by the extraction unit 57. The pulp is then pumped from the extraction unit 57, via conduit 58, to washer 59 and to peroxide unit 61 of the final bleaching stage 60. From the peroxide unit 61, the pulp is pumped to washer 62 and via conduit 63 to a chlorine dioxide unit 64. Finally, the brightened pulp is piped via conduit 65 to a bleached pulp storage unit 70. The bleached pulp is subsequently used as the raw material in the production of the finished paper product. It will be well understood by those skilled in the art that the bleaching process explained above can consist of more than the three bleaching stages shown in this example and that the present invention can be applied equally to a bleaching process having more than three stages of process.

The bleaching of the pulp dissolves any remaining lignin and renders white the remaining cellulose fibers. The intensity of whiteness and the term that the final paper product remains white are dependent on the remaining residual lignin in the cellulose fibers. It was, therefore, customary in prior art solutions to test either the lignin content of the cooking liquors or the pulp during the bleaching process as a determination of the measure of the effectiveness of the bleaching. The test of the lignin content can be used to determine the amount of bleaching agent that must be introduced into the various stages of the process to achieve the required brightness or whiteness of the pulp or, alternatively, the amount of time that the pulp must be kept in the bleaching process to achieve the desired brightness result.

The apparatus of the present invention measures the reflectance of the pulp during the bleaching process, also expressed as the whiteness of the pulp, as the means for determining the effectiveness of the ongoing bleaching process. Because the apparatus of the present invention tests the pulp in-situ, continually, on a real-time basis, its output signals can be readily applied to a system that can translate the received output signals into one of many forms of measurement standards used in the industry, such as TAPPI T236 cm-85, CPPA G.18 or SCAN C 1:77. For example, the Kappa number standard is defined as the number of milliliters of 0.1 normal potassium permanganate ($KMnO_4$) consumed by one gram of unbleached, moisture-free pulp during a specific reaction time under specific conditions. The Kappa number measures the lignin content of the incoming pulp and, therefore, how much work must be done in bleaching. The Kappa number can be visually displayed to a human operator via an output device such as an alphanumeric or chart display or printer. Additionally, the Kappa number can be expressed as data or a process variable to an automated process control system associated with the bleaching process. The system can control the introduction of bleaching agents to the bleaching stage in accordance to the measured Kappa number. Additionally, since the measure is continuous, many small adjustments to the bleaching process can be made rather than fewer larger adjustments, leading to a finer, more robust control of the process.

Figure 2:
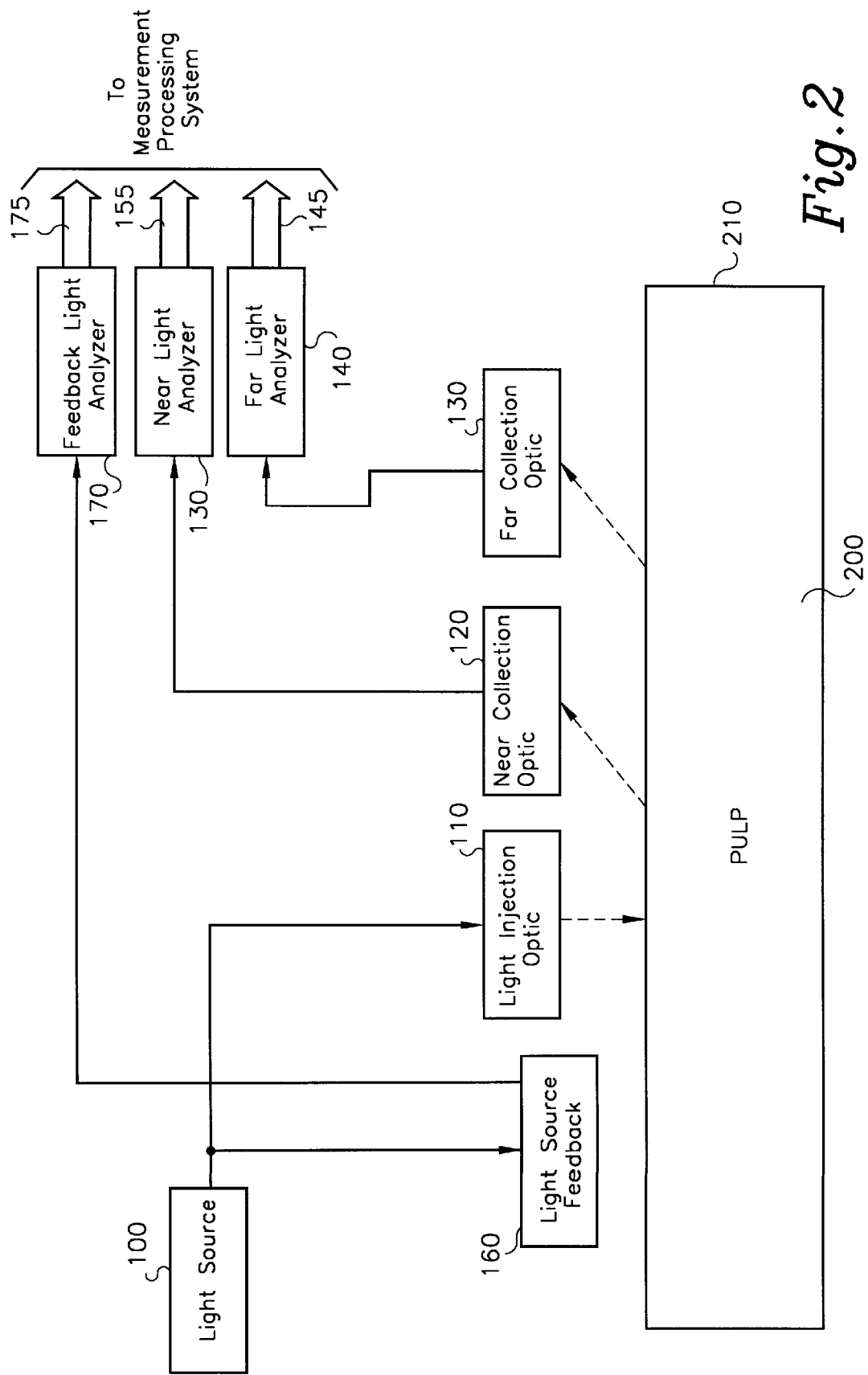
FIG. 2 is a schematic block diagram of the operational concept of the apparatus the present invention.

Turning now to FIG. 2 of the included drawings, the operational concept of the apparatus of the present invention is illustrated. Light energy having at least the blue, green, amber and infrared wavelengths is produced and emitted by a light source 100 and is delivered to the pulp 200, or an undiluted sample of pulp, by light injection optics 110. The light source 100 can be a quartz halogen bulb, or any one of the many devices known by those skilled in the art, that can produce and emit light energy in at least the above-mentioned spectra of wavelengths. The pulp 200 is typically conveyed through a pipe or conduit 210 that forms a part of the overall plant bleaching process. For example, with renewed reference to FIG. 1, the present invention can be used to sample the pulp flowing in conduit 44 after the $O_2$ delignification unit 42, or in conduit 54 after oxidation unit 52, to produce output signals to determine a Kappa number that represents the residual lignin remaining in the pulp. Additionally, the present invention can be used to sample the pulp in conduits 58, 61, and 65, thereby producing output signals that can be used to determine the brightness of the ongoing bleaching stage and, therefore, the quality of pulp 200. Alternatively, conduit 210 can comprise a bypass line from any of the bleaching process conduits that convey a portion of the total pulp taken from the aforementioned conduits.

Some of the injected light energy is absorbed by the pulp and some reflected (thus it is re-radiated) with a high correlation to the pulp properties. The light energy reflected by pulp 200 is collected by near-collection optic 120 and far-collection optic 130 and is delivered to near-light analyzer 140 and far-light analyzer 150, respectively. The near-light analyzer 140 and far-light analyzer 150 detect and measure the intensity of each of the wavelengths of light energy reflected off the pulp 200 and collected by their respective collection optics 120 and 130. Near-light analyzer 140 and far-light analyzer 150 produce output signals 145 and 155 respectively, representing the intensity of the light energy received in each wavelength by each light analyzer 140, 150.

In order to provide a baseline of the intensity of each wavelength produced by the light source 100, the present invention includes a light source feedback arrangement. The light energy produced by light source 100 is further delivered to a light source feedback arrangement 160, which is located proximate the pulp 200. The light energy is then conveyed from the feedback arrangement 160 to a feedback light analyzer 170. The feedback light analyzer 170 detects and measures the intensity of each of the wavelengths of light energy produced by the light source 100 and produces output signals 175, representing the intensity of the light energy produced by light source 100. The feedback arrangement can also be used to ascertain a drop-off of the light energy intensity produced by light source 100, due to its failure or imminent failure.

The output signals produced by light analyzers 140, 150 and 170 are applied to a measurement processing system (not shown) for translation into one of many forms of measurement standards used in the industry, such as the measurement processing system taught by co-pending application Ser. No. 08/XXX,XXX, titled, "A Continuous In-Line Kappa Measurement System"; and co-pending U.S. application Ser. No. 08/XXX,XXX, titled, "A Method for Producing Continuous In-Line Kappa Measurements for Paper-making Pulps"; both applications assigned to the assignee of the present invention and which are incorporated herein by reference.

Figure 3:
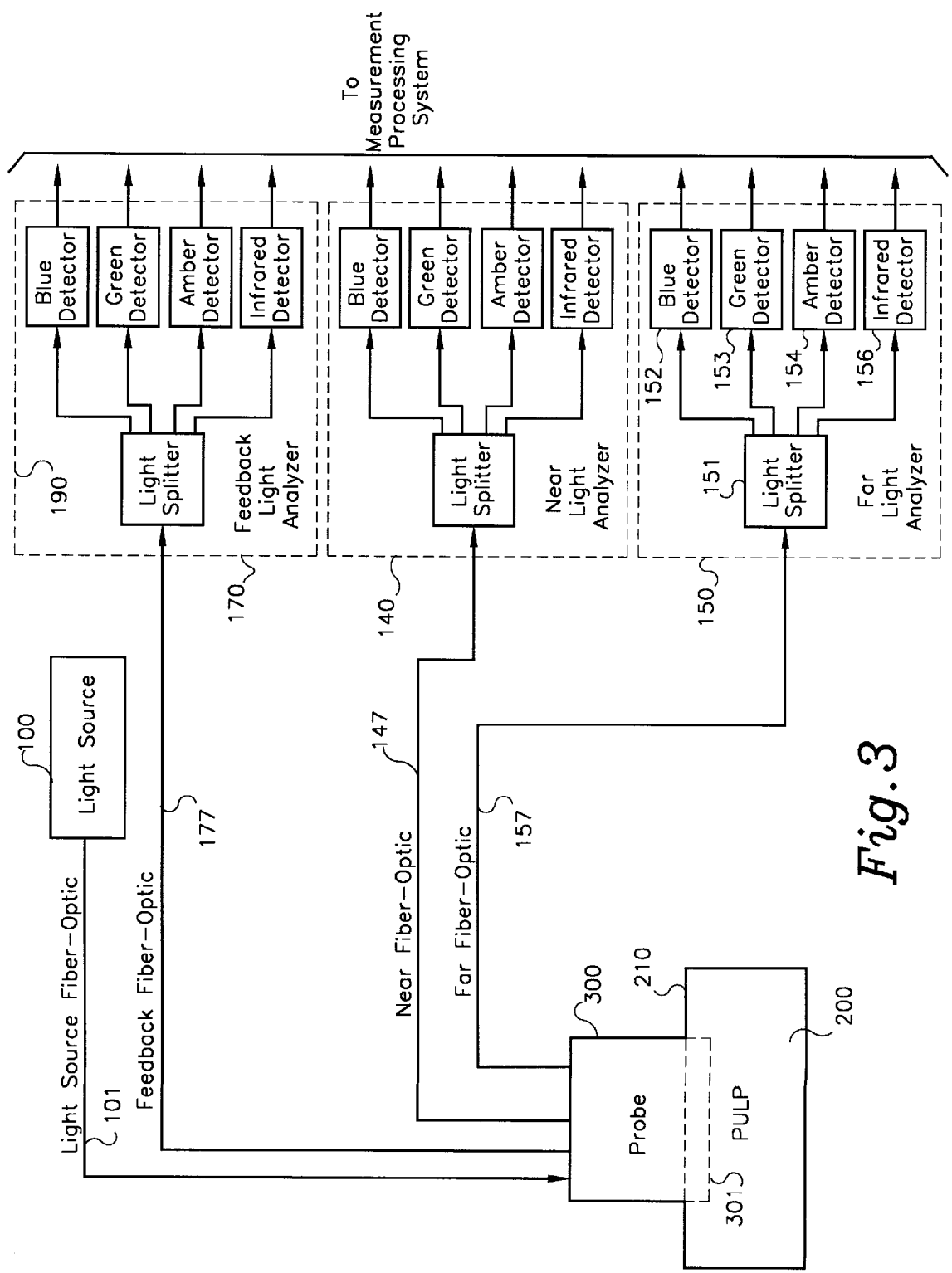
FIG. 3 is a schematic block diagram illustrating the major components used to advantage in determining the condition of completion of a papermaking pulp process in accordance to the present invention.

Turning now to FIG. 3 of the included drawings, the major components used to advantage in determining the degree of completion of a papermaking pulp process in accordance to the present invention are illustrated. The components shown in FIG. 3 include a light source 100, a probe 300, a light analyzer array 190 including a near-light analyzer 140, a far-light analyzer 150, and a feedback light analyzer 170.

Figure 4:
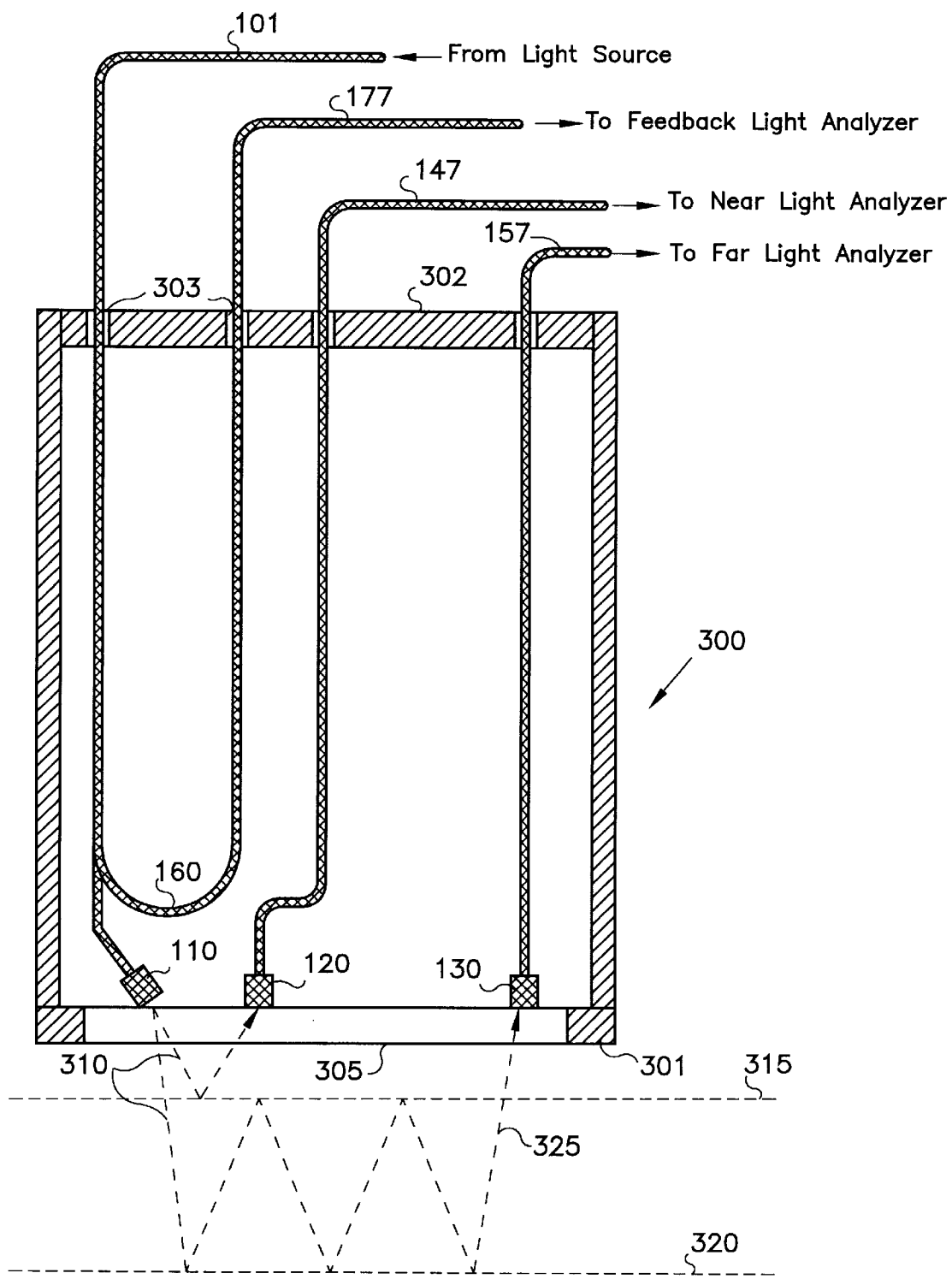
FIG. 4 is a representation of the probe and injection and collection optics in accordance to the present invention.

Before entering into a detailed explanation of the interconnection of the abovementioned components, a detailed descriptive explanation of probe 300 will first be made. Turning now to FIG. 4 of the included drawings, the probe 300 in accordance to the present invention is illustrated. The probe 300 is configured as a housing having exterior walls extending vertically along its periphery from a sealed bottom surface 301 to a top surface 302. The exterior walls and surfaces 301 and 302 define therebetween an interior space arranged to house therein light injection optic 110, near-collection optic 120, far-collection optic 130, and light source feedback arrangement 160. Bottom surface 301 includes a transparent window 305 that extends through bottom surface 301 and substantially embodies bottom surface 301. Window 305 can be made of a sapphire, quartz, or other durable transparent material. The top surface 302 includes a plurality of openings 303 arranged to allow passage of light conduction devices to the interior spaces of the probe 300.

Alternatively, three smaller transparent windows extending through surface 301 can be used. Each window would extend through surface 301 and be composed of the same durable transparent material used for window 305. A first window would be associated with the injection optic 110 and the second and third windows associated with near-collection optic 120 and far-collection optic 130 respectively. For purposes of this embodiment only the single window 305 shown in FIG. 4 will be used in the explanation of the invention. However, it will be understood by those skilled in the art that the principles of operation can be equally applied to an apparatus employing multiple windows and the invention is not limited thereto.

With renewed reference to FIG. 3 as well as FIG. 4, probe 300 is arranged to be inserted into conduit 210 sufficiently to allow bottom surface 301 to enter the conduit and allow window 305 to be substantially immersed into pulp 200. Broad spectrum light energy having at least the blue, green, amber and infrared wavelengths is produced and emitted from light source 100. The light energy emitted by light source 100 is conducted to probe 300 via a light source fiber-optic 101. Fiber-optic 101, as well as fiber-optics 147, 177 and 157, can be either a single-mode fiber cable having only one light-energy-carrying conductor or a multi-mode fiber cable having a plurality of light conductors bundled together. Light source fiber-optic 101 enters probe 300 via one of openings 303 and extends into the interior of probe 300 and is terminated above window 305. The termination end of fiber-optic 101 forms injection optic 110. The light energy produced by light source 100 is injected into pulp 200 through window 305 as shown by line 310. Any of the means known by those skilled in the art for forming injection optic 110 can be employed that allow for the transmission of the maximum amount of light energy to pulp 200. For example, the injection optic 110 can be formed by mounting the end of the fiber-optic 101 on the top surface of window 305, or attaching it to a lens, or system of lenses, or other similar devices that can couple and/or amplify the injection of the light energy. Additionally, light injection optic 110 is mounted at a 30 degree angle facing the near-collection optic 120 and far-collection optic 130. This angular displacement provides a directional focusing of the light injected into the pulp, leading to increased light collection performance. Light energy injected into the pulp 200, shown generally by line 310, and not absorbed, is re-radiated or reflected by the pulp and enters probe 300 via window 305 and collected by near-collection optic 120 for a near reflection. For a far reflection, the reflected light enters farther along window 305 and is collected by far-collection optic 130. As can be seen in FIG. 4, the light energy reflected near the injection optic 110 is scatter reflected by the pulp and normally travels above a boundary layer 315. This scatter reflection illustrated by line 315 enters window 305 and is collected by near-light collection optics 120. The end of near fiber-optic 147 is terminated above window 305, forming the near-collection optic 120. The end of fiber-optic 147 is situated over window 305 so as to maximize the coupling of the light energy collected through window 305. As with light injection optics 110, near-collection optic 120 can use any manner of fiber-optic end termination techniques that allow the efficient coupling of the light entering window 305. Light collected by the near-collection optic 120 is conveyed by fiber-optic 147 to the near-light analyzer 140.

A portion of the light energy injected into the pulp 200 penetrates boundary layer 315 and is reflected between boundary layers 315 and 320 as illustrated by line 325. This light energy enters window 305, where it is collected by far-collection optic 130. The end of a far fiber-optic 157 is terminated above window 305, forming the far-collection optic 130. The end of fiber-optic 157 is situated over window 305 so as to maximize the coupling of the light energy collected through window 305 to fiber-optic 157. As with the near-collection optic 120, far-collection optic 130 can use any manner of fiber-optic end termination techniques that allow the efficient coupling of the light energy entering window 305. Light collected by far-collection optic 130 is conveyed by fiber-optic 157 to the far-light analyzer 150.

Light source feedback arrangement 160 is comprised of a fiber-optic shunt that couples the light energy transmitted by light source fiber-optic 101 to a feedback fiber-optic 177. Light energy traveling through fiber-optic 101 is split off near injection optics 110 and is returned by fiber-optic 177 to feedback light analyzer 170.

Each of the light analyzers 140, 150 and 170 of light analyzer array 190 are solid state devices and are comprised of the same major components. Only the components of the far-light analyzer 150 will be used in the following explanation. It will be appreciated by those skilled in the art that the other light analyzers operate in the same manner as the one described below. Light conveyed by the far fiber-optic 157 enters far-light analyzer 150 and is split into four equal light energy segments by light splitter 151. Each segment includes all of the originally collected wavelengths and wavelength intensities. Each segment is coupled to a respective one of a blue wavelength detector 152, green wavelength detector 153, amber wavelength detector 154 and infrared wavelength detector 156. Each wavelength detector 152, 153, 154 and 156 acts as an optical bandpass filter, passing its respective light energy wavelength to an included photo-detector that produces an output signal voltage that is representative of the intensity of the light energy wavelength received. Each output signal produced by a respective detector 152, 153, 154 and 156 is transmitted to a measurement processing system for processing of the information received. Another method that can be effectively used to convert the received light energy into representations of the intensity of the wavelengths received is to substitute a prism or any other like device for light splitter 151. The prism can divide the received light energy into distinct wavelengths and the intensity of the blue, green, amber and infrared wavelengths measured by an associated photo-detector, thereby producing an output signal voltage representative of the intensity of each wavelength received. When a multi-mode fiber-optic is employed, the individual optical fibers can be equally divided to couple an equal amount of optical fibers to each of the four wavelength detectors, effectively performing the light splitter 151 function. It will be appreciated by those skilled in the art that other means of beam splitting and wavelength detecting can be used to convert the light energy received into output signals representing the intensity of each received wavelength, and the invention is not limited thereto.

In order to moderate the accumulation of pulp deposits on window 305, which deposits would adversely affect the performance of the apparatus, the probe can be inserted into the conduit at an angle facing the pulp flow (not shown). This angled mounting allows bottom surface 301 to have a more direct contact with the pulp traveling in the conduit 210. This allows the pulp 200 to flow more forcefully over surface 301 and window 305 thereby, minimizing deposit formations.

Even though the apparatus of the present invention illustrated in FIG. 3 is shown comprised of three distinct assemblies, comprising a probe 300 including a light injection optic 110, near-collection optic 120, far-collection optic 130, and light source feedback arrangement 160 housed therein, an analyzer array 190 including solid state analyzers 170, 140, and 150 and a light source 100 all optically coupled to the probe 300 by fiber-optic conduits, it will be appreciated by those skilled in the art that the apparatus can also be assembled in other variations. One variation could have all of the aforementioned components housed within the probe 300, or the light source 100 and light analyzer array 190 housed together in a separate enclosure.

The present invention has been described with particular reference to the preferred embodiments thereof. It will be obvious that various changes and modifications can be made therein without departing from the spirit and scope of the invention as defined in the appended claims and characterised by an apparatus that develops output signals representing the degree of finished state of a processed medium during a process operation by injecting broad spectrum light energy from a light energy source into the processed medium and collecting the resultant reflected light energy from a first light collector located near the point of injection and a second light collector located far from the point of injection. The light energy is conveyed to a respective light analyzer associated with each light collector and analyzed by dividing the detected light into distinct spectral wavelengths to generate output signals representing the intensity of light energy received in each wavelength. A feedback arrangement conducts the light energy emitted by the light source to a location proximate the point of injection and then to an associated light analyzer that divides the light emitted by the light source into distinct spectral wavelengths and generates output signals representing the intensity of the light energy emitted by the light source in each wavelength.

What is claimed is:

1. An apparatus for developing output signals utilized in the determination of the degree of the finished state of a processed medium, said apparatus comprising:

a light source for generating light energy in a plurality of wavelengths;

a light energy conduction device for conveying said light energy from said light source and for injecting said light energy into said processed medium;

a first light collection device for collecting said light energy reflected by said processed medium from a first location;

a second light collection device for collecting said light energy reflected by said processed medium from a second location;

a first light analyzer connected to said first light collection device, said first light analyzer arranged to determine the intensity of each wavelength of light energy received and to generate a plurality of first output signals indicative thereof;

a second light analyzer connected to said second light collection device, said second light analyzer arranged to determine the intensity of each wavelength of light energy received and to generate a plurality of second output signals indicative thereof;

a feedback device for returning said light energy conveyed by said light energy conduction device from a location proximate said processed medium; and a third light analyzer connected to said feedback device, said third light analyzer arranged to determine the intensity of each wavelength of light energy received and to generate a plurality of third output signals indicative thereof whereby said first, said second and said third output signals are used in the determination of the degree of finished state of said processed medium.

2. The apparatus as claimed in claim 1, wherein said processed medium is contained within a conduit and said apparatus further includes a housing, said housing extending into said conduit and said housing including a first surface having at least one transparent window being substantially immersed into said processed medium, whereby said light energy conduction device injects said light energy into said processed medium through said transparent window.

3. The apparatus as claimed in claim 2, wherein said first light collection device is located at a first distance from said light energy conduction device and said light energy reflected by said processed medium enters said transparent window and is collected by said first light collection device and is conveyed to said first light analyzer.

4. The apparatus as claimed in claim 3, wherein said second light collection device is located at a second distance from said light energy conduction device and said light energy reflected by said processed medium enters said transparent window and is collected by said second light collection device and is conveyed to said second light analyzer.

5. The apparatus as claimed in claim 4, wherein said second distance is greater than said first distance.

6. The apparatus as claimed in claim 1, wherein said light source is a halogen lamp that generates and emits light that includes at least the blue, green, amber and infrared wavelengths.

7. The apparatus as claimed in claim 6, wherein said first light analyzer includes a plurality of wavelength detectors, each wavelength detector arranged to detect one of said blue, green, amber and infrared wavelengths and to produce a respective one of said plurality of first output signals representing the intensity of the respective wavelength received.

8. The apparatus as claimed in claim 6, wherein said second light analyzer includes a plurality of wavelength detectors, each wavelength detector arranged to detect one of said blue, green, amber and infrared wavelengths and to produce a respective one of said plurality of second output signals representing the intensity of the respective wavelength received.

9. The apparatus as claimed in claim 6, wherein said third light analyzer includes a plurality of wavelength detectors, each wavelength detector arranged to detect one of said blue, green, amber and infrared wavelengths and to produce a respective one of said plurality of third output signals representing the intensity of the respective wavelength received.

10. The apparatus as claimed in claim 1, wherein said feedback device collects said light energy from said light conduction device immediately prior to said light energy being injected into said processed medium.

11. The apparatus as claimed in claim 2, wherein said light energy conduction device is angularly mounted over said transparent window to inject said light energy into said processed medium in the direction of said first and said second light collection devices.

* * * * *